United States Patent [19]

Chang

[11] Patent Number: 4,510,127

[45] Date of Patent: Apr. 9, 1985

[54] COMPOSITIONS AND METHOD FOR REDUCING ELUTION OF THERAPEUTIC AGENTS FROM TEETH

[75] Inventor: Robert W. H. Chang, Shoreview, Minn.

[73] Assignee: Minnesota Mining and Manufacturing Company, St. Paul, Minn.

[21] Appl. No.: 424,579

[22] Filed: Sep. 27, 1982

Related U.S. Application Data

[60] Division of Ser. No. 303,206, Sep. 18, 1981, Pat. No. 4,366,146, which is a division of Ser. No. 176,680, Aug. 11, 1980, Pat. No. 4,304,766, which is a division of Ser. No. 26,402, Apr. 2, 1979, Pat. No. 4,243,658, which is a continuation-in-part of Ser. No. 865,681, Dec. 29, 1977, abandoned.

[51] Int. Cl.³ .............................................. A61K 7/18
[52] U.S. Cl. ...................................... 424/52; 424/49; 424/57
[58] Field of Search ..................... 424/49–58

[56] References Cited

U.S. PATENT DOCUMENTS

| 2,580,473 | 1/1952 | Sowa et al. | 424/184 |
|---|---|---|---|
| 2,809,990 | 10/1957 | Brown | 562/556 |
| 2,829,086 | 4/1958 | Kirschenbauer | 424/52 |
| 2,955,985 | 10/1960 | Kuna | 424/52 |
| 3,029,191 | 4/1962 | King | 424/58 |
| 3,120,469 | 2/1964 | Tamas | 424/49 |
| 3,429,963 | 2/1969 | Shedlovsky | 424/56 |
| 3,431,208 | 3/1969 | Bailey | 424/49 |
| 3,507,955 | 4/1970 | Osipow | 424/54 |
| 3,624,120 | 11/1971 | Yetter | 424/184 |
| 3,751,568 | 8/1973 | Mundorff et al. | 424/52 |
| 3,956,480 | 5/1976 | Dichter et al. | 424/78 |
| 3,969,499 | 7/1976 | Lee et al. | 424/52 |

FOREIGN PATENT DOCUMENTS 2164383  8/1972  Fed. Rep. of Germany .

OTHER PUBLICATIONS

A.D.A. Accepted Dental Therapeutics, 35th Ed. (1973), pp. 214–217 and 222–223.

Primary Examiner—Richard A. Schwartz
Attorney, Agent, or Firm—Donald M. Sell; James A. Smith; James V. Lilly

[57] ABSTRACT

A dentifrice composition containing a water-dispersible, membrane-forming material which, when applied to tooth surfaces in an oral environment, attaches thereto and forms a substantially continuous, hydrophobic barrier thereon which substantially reduces elution of a previously applied therapeutic agent.

6 Claims, No Drawings ns and Method for Reducing Elution of Therapeutic Agents from Teeth

CROSS REFERENCE TO RELATED APPLICATION

This application is a division of Ser. No. 303,206 filed Sept. 18, 1981, now U.S. Pat. No. 4,366,146, which was a division of Ser. No. 176,680 filed Aug. 11, 1980, now U.S. Pat. No. 4,304,766, which was a division of Ser. No. 026,402 filed Apr. 2, 1979, now U.S. Pat. No. 4,243,658, which was a continuation-in-part of Ser. No. 865,681 filed Dec. 29, 1977, now abandoned.

BACKGROUND OF THE INVENTION

This invention relates to compositions for topical application to teeth. More particularly it relates to compositions and methods which substantially reduce the elution of a previously applied therapeutic agent from teeth. The compositions and methods of the invention are especially useful in inhibiting the growth of cariogenic bacteria and preventing the formation of plaque on teeth in an oral environment.

Dental plaque results when cariogenic bacteria (e.g., *Streptococcus Mutans*) collect in colonies and form deposits on tooth surfaces. The presence of the bacteria and deposits is extremely detrimental to the health of the tooth for, if left unchecked, they may result in infected gingival tissue, the formation of dental caries and possibly periodontal disease. In extreme cases their presence may even result in the loss of teeth.

Many attempts have been made to control or prevent both the occurrence of dental caries and the formation of dental plaque. For example, fluoride solutions or gels have been used. Treatment with these materials is typically performed in a dental office at periodic, but not frequent, intervals. Such treatments are primarily intended to render tooth enamel more resistant to the acid action caused by plaque. They do not, however, result in plaque control for an extended period since plaque reestablishes itself on the teeth shortly after ingestion of food.

Even when the frequency of application of such solutions and gels is increased only partial control has been shown. For example, studies wherein a fluoride-containing solution (1% fluoride concentration) was applied four to five times in the course of a year have demonstrated that this technique had only limited success due to the rapid reestablishment of plaque in the oral cavity. Moreover, the daily application of a fluoride gel by means of a custom-fitted polyvinyl mouthpiece for a period of twenty-one months also showed no substantial change in plaque formation among treated and untreated patients. See "Clinical Anticaries Effect of A Repeated Sodium Fluoride Application by Mouthpiece", Journal of the American Dental Association, V. 75, No. 3, September, 1967, pages 638–644.

As a result, there has been no truly effective prophylactic treatment for teeth made available. However, the present invention provides such a treatment.

SUMMARY OF THE INVENTION

In accordance with the present invention there is provided a dentifrice composition for substantially reducing elution of a previously applied therapeutic agent from teeth, said composition comprising:

at least one ingredient selected from the group consisting of therapeutic agents, polishing agents, surfactants, flavoring agents, sweetening agents, thickening agents and humectants, and at least about 0.05% by weight, and preferably from about 0.1 to 5% by weight, of a water-dispersible, membrane-forming material which, when applied to the surface of teeth in an oral environment, forms a substantially continuous hydrophobic barrier thereon which substantially reduces the elution of said previously applied therapeutic agent from said tooth.

In another embodiment of the present invention there is provided a method for inhibiting plaque formation on teeth which comprises contacting the teeth with an effective amount of the above-described composition.

As they are used herein, the following terms have the following meanings:

Dentrifrice Compositions

Compositions for topical application to the teeth such as mouthwashes or rinses, toothpastes, gels, etc.

Water Dispersible Materials

Materials which may be either dispersed or dissolved in aqueous media at a level of at least about 10 parts of such material per one million parts of media (i.e., 0.001%), and preferably at a level of at least about 100 parts of such material per one million parts of media (i.e., 0.01%).

Hydrophobic Barrier

A layer which does not adsorb or absorb water.

The present invention provides a simple and effective composition and process by which cariogenic bacteria and plaque formation may be controlled. The barrier formed by compositions of the invention substantially reduces the elution of a previously applied therapeutic agent (e.g., dental fluoride treatments), thereby prolonging the effectiveness of such agents. Moreover, compositions of the invention need be applied only periodically (e.g., once daily) in order to achieve the desired reduction in elution and resultant control of caries and plaque.

DETAILED DESCRIPTION OF THE INVENTION

A variety of membrane-forming materials are useful in the present invention. They include polymeric and nonpolymeric, ionic and nonionic materials. Ionic materials are those which when provided in aqueous solution, are attracted to either the positive or negative electrode during electrolysis. Thus, anionic materials are attracted to the positive electrode and cationic materials are attracted to the negative electrode. Nonionic materials are those materials which, when provided in aqueous solution, are not normally attracted to either the positive or negative electrode during electrolysis.

Anionic Membrane-Forming Materials

Anionic membrane-forming materials useful in the present invention are believed to attach to tooth surfaces and form a substantially continuous barrier thereon by complexing with calcium present in the teeth. The strength of the complex structure formed may be represented by the formation constant of the complexing agent. This constant is expressed in terms of $\log_{10} K$ and is based upon the complex formed between the membrane-forming material and a ligand on the tooth surface. The formation constant is measured at about 25° C. and an ionic strength approaching 0 from the following equation:

$$W + L \rightleftharpoons WL$$

$$K = \frac{[WL]}{[W][L]}$$

In these formulae W represents the membrane-forming material, L represents the ligand which complexes with W and WL represents the complex formed between W and L. The bracketed symbols indicate the concentration of the indicated material at equilibrium.

The formation constant of useful anionic membrane-forming materials is in the range of about 0.5 to 8. Preferably, it is in the range of about 0.6 to 6. A formation constant greater than 8 indicates a very strong calcium complexor. Such complexors tend to decalcify the tooth (i.e., withdraw the calcium from the tooth), thereby weakening its resistance to disease and wear.

Polymeric Anionic Membrane-forming Materials

The polymeric anionic membrane-forming materials useful in the present invention comprise a class of polymers having a polyolefinic main chain with acidic functionalities pendant therefrom. Typical of the materials which can comprise the polyolefinic main chain are polymers of ethylene, propylene, styrene, unsaturated carboxylic acids, (especially those containing up to about 5 carbon atoms) and copolymers of two or more of these materials.

The acid functionalities pendant from the polyolefinic main chain are selected from

—COOM,

—PO(OM)$_2$

—OPO(OM)$_2$

—SO$_3$M

—OSO$_3$M, wherein M is selected from hydrogen, alkali metal (e.g., sodium, potassium, lithium, etc.), ammonium and amine groups.

Representative polymeric anionic membrane-forming materials useful in the present invention are:

(a) Polyacrylic acid, having the repeating unit $$+CH_2-CH\frac{}{}_n,$$
$$\quad\quad |$$
$$\quad\quad COOH$$

a molecular weight in the range of 2,000 to 4,000,000, available from the Aldrich Chemical Company;

(b) "Separan AP 30", having the repeating unit $$+CH_2-CH-CH_2-CH\frac{}{}_n$$
$$\quad\quad |\quad\quad\quad\quad |$$
$$\quad\quad CONH_2\quad COONa$$

and a molecular weight of about 2,000,000, available from the Dow Chemical Company;

(c) sodium polystyrenesulfonate, having the repeating unit $$+CH_2-CH\frac{}{}_n$$
$$\quad\quad |$$
$$\quad\quad \text{(phenyl)}$$
$$\quad\quad |$$
$$\quad\quad SO_3Na$$

and a molecular weight in the range of about 5,000 to 6,000,000, available from the Dow Chemical Company;

(d) "Gantrez AN", having the repeating unit $$\quad\quad\quad O$$
$$\quad\quad/\quad\backslash$$
$$O=C\quad\quad C=O$$
$$\quad |\quad\quad\quad |$$
$$+CH_2CH-CH----CH\frac{}{}_n$$
$$\quad |$$
$$\quad OCH_3$$

available from GAF Corporation;

(e) "EMA" polymers, having the repeating unit $$\quad\quad\quad O$$
$$\quad\quad/\quad\backslash$$
$$O=C\quad\quad C=O$$
$$\quad |\quad\quad\quad |$$
$$+CH_2-CH_2-CH----CH\frac{}{}_n$$

available from the Monsanto Chemical Company;

(f) Polyvinyl phosphate, having the repeating unit $$+CH_2-CH\frac{}{}_n$$
$$\quad\quad |$$
$$\quad\quad OPO(OH)_2$$

commercially available from Polysciences, Incorporated; and (g) copolymers of acrylates which contain pendant carboxyl groups, such as the "Carboset" resins available from the B. F. Goodrich Chemical Company.

Nonpolymeric Anionic Membrane-Forming Materials

The nonpolymeric anionic membrane-forming materials useful in the present invention comprise a class of materials having a nonionic aliphatic portion and an anionic terminal group. They may be generally represented by the formula R$^1$Z wherein R$^1$ is the aliphatic portion of the compound and Z is the anionic terminal group.

The aliphatic portion may be saturated or unsaturated and it may be straight or branched chain. Additionally, it may be a hydrocarbon or fluorocarbon radical. Moreover, the aliphatic portion may contain hetero atoms selected from oxygen, nirogen and sulfur.

Z may be joined directly to R' or, alternatively, there may be a divalent linking group Q which joins R' and Z. Q must not interfere with the formation of the complex structure between the anionic material and the tooth surface.

The Z groups useful in the nonpolymeric membrane forming materials are selected from

—COOM

—PO(OM)$_2$

=POOM

—OPO(OM)$_2$

—SO$_2$OM

—OSO$_2$OM

—PS(SM)$_2$

=PSSM wherein M is as defined previously.

Representative of useful Q groups are hydrocarbon groups containing from 1 to about 30 carbon atoms, oxygen, sulfur and —SO$_2$O—. The hydrocarbon groups may be straight chain or branched chain and may include unsaturation and aromatic (e.g., cyclic) groups. Moreover, the hydrocarbon groups may contain heteroatoms in the skeletal chain. Typically the hetero atoms are selected from the group consisting of oxygen, nitrogen and sulfur.

A number of nonpolymeric anionic materials are useful as the membrane-forming material. One group of such materials contains substantial quantities of fluorine in the main chain. Thus, for example, the perfluoroalkanesulfonamidoalkyl esters of phosphorous acids have been found useful. These compounds have the formula $$[R_fSO_2N(R^2)R^3O]_mPX(XB)_{3-m} \quad (I)$$

wherein $R_f$ is a monovalent, stable, inert, fluorinated, saturated aliphatic nonpolar radical; $R^2$ is hydrogen, alkyl of from 1 to 6 carbon atoms, aryl, cycloalkyl, aralkyl or alkaryl; $R^3$ is an alkylene, arylene, alkarylene or aralkylene bridging group containing from 1 to 12 carbon atoms, m is 1 or 2; X is oxygen or sulfur; and B is hydrogen, alkyl, aryl, cycloalkyl, alkaryl, or aralkyl (each of up to 20 carbon atoms) alkali metals (e.g., sodium, potassium, lithium, etc.), ammonium, or amine groups.

The $R_f$ radical can be straight chain, branched chain or, if sufficiently large, cyclic. Additionally, it can be a combination of cyclic, branched and straight chain, (e.g., alkylcycloaliphatic). The skeletal chain of the $R_f$ radical can include catenary oxygen and/or trivalent nitrogen hetero atoms bonded only to carbon atoms. Such hetero atoms provide stable linkages between fluorocarbon groups and do not interfere with the inert character of the radical.

The $R_f$ radical has from about 4 to 16 carbon atoms; preferably from about 6 to 12 carbon atoms; and most preferably 8 carbon atoms. Moreover, $R_f$ generally contains from about 40 to 80 weight percent, and preferably from about 50 to 80 weight percent, fluorine. Correspondingly the fluorochemical material of formula I will contain from about 4 to 70 weight percent fluorine.

The most preferred $R_f$ radicals are fully or substantially fully fluorinated. Thus they are perfluoroalkyl groups (e.g., $C_nF_{2n+1}$—). Additionally the terminal portion of the $R_f$ group preferably contains a —CF$_3$ group, and most preferably the terminal portion also has at least three fully fluorinated carbon atoms, (e.g., CF$_3$CF$_2$CF$_2$—).

$R^2$ may be hydrogen or a straight or branched chain alkyl, aryl, cycloalkyl, alkaryl or aralkyl group. Preferably, it is a straight chain alkyl group containing 2-3 carbon atoms.

$R^3$ is an divalent bridging group. It may be straight chain or branched chain and preferably is an alkylene group that contains from 2 to 8 carbon atoms.

Representative examples of useful perfluoroalkanesulfonamidoalkyl esters of phosphorous acids useful in the present invention include

[C$_8$F$_{17}$SO$_2$N(C$_2$H$_5$)C$_2$H$_4$O]$_2$PSSH

[C$_8$F$_{17}$SO$_2$N(C$_2$H$_5$)C$_2$H$_4$O]$_2$POOH

C$_8$F$_{17}$SO$_2$N(C$_2$H$_5$)C$_2$H$_4$OPO(OH)$_2$

C$_8$F$_{17}$SO$_2$N(C$_2$H$_5$)C$_{10}$H$_{20}$OPO(OH)$_2$

C$_8$F$_{17}$SO$_2$N(C$_2$H$_5$)C$_2$H$_4$OP(OH)(O)OC$_{18}$H$_{37}$

C$_8$F$_{17}$SO$_2$N(C$_4$H$_9$)C$_2$H$_4$OPO(OH)$_2$

The preparation of these compounds is described in U.S. Pat. No. 3,094,547 (for those wherein X is oxygen). Thus the appropriate perfluoroalkyl alcohol may be reacted with phosphorous oxytrichloride above 50° C. to produce the corresponding dichloride. The dichloride may, in turn, be hydrolyzed to produce the phosphate.

The preparation of these compounds when X is sulfur is also known and may be carried out by reacting the appropriate perfluoroalkyl alcohol with phosphorous pentasulfide followed by refluxing in a non-reactive solvent such as benzene or isopropyl ether. Additional details on the preparation of dithiophosphate esters may be found in Inorganic Synthesis, Vol. 6, p. 142, (McGraw-Hill, 1960).

Yet another nonpolymeric anionic fluorochemicals useful as the membrane-forming material are the fluoroalkanephosphates which may be represented by the formula $$[C_gF_{2g+1}CH_2O]_kPO(OM)_q \quad (II)$$

wherein M is selected from hydrogen, alkali metal (e.g., sodium, potassium, lithium), ammonium and amine groups, and g is an integer of from 1 to 10, k is 1 or 2 and q is 3-k. These materials are commercially available from E. I. duPont de Memours as "Zonyl FSP".

Another class of nonpolymeric anionic materials useful in the present invention is the perfluoroalkanesulfonamidoalkyl carboxylic acids of the formula $$R_fSO_2N(R^2)R^3COOM \quad (III)$$

wherein $R_f$, $R^2$ and $R^3$ are as defined in formula I and M is as defined in formula II. The preparation of these compounds is described in U.S. Pat. No. 2,809,990. Thus the appropriate perfluoroalkanesulfonamide may be converted to a sulfonamide salt which may then be converted to an ester of the desired acid which may in turn be hydrolyzed to the acid or the salt.

Representative examples of perfluoroalkanesulfonamidoalkyl carboxylic acids useful in the present invention include

C$_8$F$_{17}$SO$_2$N(CH$_3$)(CH$_2$)$_{10}$COOH

C$_8$F$_{17}$SO$_2$N(C$_2$H$_5$)CH$_2$COOH

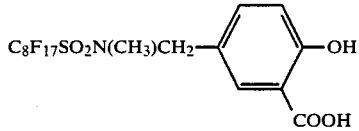

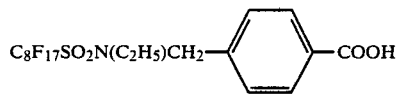

Yet another class of nonpolymeric fluorochemicals useful as the membrane-forming material are the fluorocarbon monocarboxylic acids of the formula

 (IV)

wherein $R_f$ is as defined in formula I and M is as defined in formula II. The preparation of these compounds is described in U.S. Pat. No. 2,567,011.

Representative examples of fluorocarbon monocarboxylic acids useful in the present invention include $C_8F_{17}COOH$ $C_{11}F_{23}COOH$ Still another class of nonpolymeric anionic fluorochemicals useful as the membrane-forming material are represented by the formula

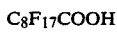 (V)

wherein $R_f$ and $R^3$ are as defined in formula I and M is as defined in formula II. These compounds are described in U.S. Pat. No. 2,951,051.

Representative examples of compounds of formula V include $C_8F_{17}CH_2CHClC_8H_{16}COOH$ $C_8F_{17}C_{10}H_{20}COOH$ Yet another class of nonpolymeric anionic fluorochemicals useful in the present invention are the perfluoroalkanesulfonate esters of the formula

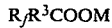 (VI)

wherein $R_f$ is as defined in formula I and Y is an aryl group. The preparation of these compounds is described in U.S. Pat. No. 3,346,612. Thus, these compounds may be prepared by reacting an appropriate phenolic compound with an appropriate perfluoroalkanesulfonyl fluoride.

Representative of useful perfluoroalkanesulfonate esters are

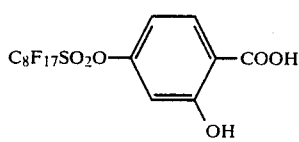

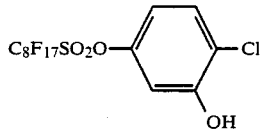

Still another class of nonpolymeric anionic fluorochemicals useful in the present invention are the fluorocarbon sulfonic acids and their derivatives. These compounds have the formula

 (VII)

wherein $R_f$ is as defined in formula I and M is as defined in formula II. The preparation of these compounds is described in U.S. Pat. No. 2,732,398. A particularly useful compound of this type is $C_8F_{17}SO_2OK$.

Nonfluorinated materials are also useful as nonpolymeric anionic materials in the present invention. One class of such materials is the carboxylic acids of the formula

 (VIII)

wherein $R^5$ is a hydrocarbon group, preferably alkyl, containing from 6 to 24 carbon atoms and M is as defined in formula II. The $R^5$ group may be straight or branched chain and may contain unsaturation. Preferably, however, the carboxylic acids are saturated. When the compositions employing materials of formula VIII as the membrane-forming material are formulated in water, the acid should be provided in its water-soluble salt form.

Representative examples of useful carboxylic acids of formula VIII include lauric, myristic, palmitic, stearic and oleic acids.

Another class of nonfluorinated material useful as the membrane-forming material comprises the organic phosphates, of the formula $[R^6O]_mPO(OM)_{3-m}$ (IX)

wherein $R^6$ is a hydrocarbon group containing from about 10 to 20 carbon atoms, M is as defined in formula II and m is 1 or 2. Representative examples of useful organic phosphates of formula IX include $(C_{16}H_{33}O)_2$-POOH and $(C_{18}H_{37}O)_2POOH$.

Still other anionic non-polymeric materials may be used as the membrane-forming material. Thus, aliphatic sulfonates of the formula

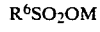 (X)

wherein $R^6$ is as defined in formula IX and M is as defined in formula II are also useful. Representative examples of useful aliphatic sulfonates include $C_{12}H_{25}SO_2ONa$ and sodium dioctyl sulfosuccinate, i.e.,

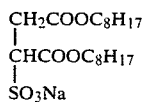

Sodium dioctyl sulfosuccinate is commercially available as "Aerosol OT" from American Cyanamide Company.

Another useful class of nonpolymeric, anionic, membrane-forming materials is the N-acyl alkylaminoalkanoic acids of the formula $$R^6CON(R^2)R^3COOM \quad (XI)$$

wherein $R^6$ is as defined in formula IX, $R^2$ and $R^3$ are as defined in formula I and M is as defined in formula II. A particularly useful alkylaminoalkanoic acid is $C_{11}H_{23}CON(CH_3)CH_2COONa$.

Yet another useful class of nonpolymeric, anionic, membrane-forming materials is the hydroxamic acids of the formula $$R^6CONHOH \quad (XII)$$

wherein $R^6$ is as defined in formula IX. Particularly useful hydroxamic acids are the fatty acid hydroxamic acids.

Amine salts of fatty acids have also been found useful as the membrane-forming material. These compounds are known and may be prepared by reacting an amine (e.g., triethanol amine) with a fatty acid (e.g., stearic acid). One particularly useful compound of this type is the triethanol amine salt of stearic acid.

Cationic Membrane-Forming Materials

Cationic membrane-forming materials useful in the present invention are believed to attach to tooth surfaces via a complexing interaction between the cationic portion of the material and the proteinaceous portion of the tooth. A variety of cationic materials may be used as the membrane-forming material. They include polymeric and nonpolymeric materials.

Polymeric Cationic Membrane-Forming Materials

The polymeric cationic membrane-forming materials useful in the invention comprise a class of polymers containing nitrogen in their backbone. They may have molecular weights as low as about 100 or higher than about 100,000.

Representative polymeric cationic membrane-forming materials are:

(a) Polydimeryl polyamine, a polydimeryl polyamide which has a molecular weight of about 8000, and an amine number of about 120 and is commercially available from General Mills Chemical Co;

(b) Polyethylene imine which has the repeating unit —$CH_2$—$CH_2$—NH—$_n$, and a molecular weight of about 100,000 and is commercially available from Dow Chemical Co.;

(c) 1,5-dimethyl diazaundecamethylene polymethobromine hexadimethrine bromide, a quaternary composition which has the repeating unit

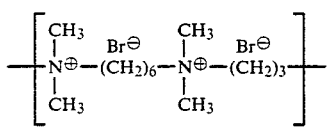

and is commercially available from Aldrich Chemical Company as Polybrene;

(d) Poly(N,N-dimethyl-3,5-dimethylenepiperidinium chloride) which has the repeating unit

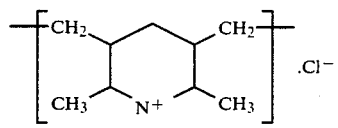

and is commercially available from Aldrich Chemical Company; and (e) "Protamine" a grouping of simple proteins which yield only amino acids, especially diamino acids, upon cleavage by enzymes or acids and is commercially available from Pfaltz and Bauer, Inc.

Nonpolymeric Cationic Membrane-Forming Materials

The nonpolymeric cationic membrane-forming materials useful in the present invention comprise a class of materials having a non-ionic aliphatic portion and a cationic terminal group. They may be generally represented by the formula $R^1D$ wherein $R^1$ is the aliphatic portion of the compound and is as defined previously and D is the cationic terminal group.

D may be joined directly to $R^1$ or, alternatively, there may be a divalent linking group Q which joins $R^1$ and D. Q must not interfere with the formation of the complex structure between the cationic material and the two surfaces and is as defined previously herein.

Representative examples of cationic terminal groups (D) useful in the present invention include

—$NHC_2H_4NHC_2H_4NH_2$

—$NH_2$

—$NHC_2H_4NH_2$

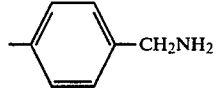

—$\overset{\oplus}{N}(CH_3)_2C_2H_4OH.H_2PO_4^{\ominus}$

—$\overset{\oplus}{N}(CH_3)_3.Cl^{\ominus}$

A number of nonpolymeric cationic materials are useful as the membrane-forming material. One group of useful materials contains substantial quantities of fluorine in the main chain. Thus, for example, the distally perfluoroalkanesulfonamido amines described in U.S. Pat. No. 3,458,571 have been found useful. These compounds have the formula $$R_fSO_2N(R^2)R^3 \, NHA \quad (XIII)$$

wherein $R_f$, $R^2$ and $R^3$ are as described in formula I and A is a proton (e.g., hydrogen) or a poly(alkylamino) group.

Representative examples of compounds according to formula XIII include $C_8F_{17}SO_2N(C_2H_5)C_2H_4NHC_2H_4NHC_2H_4NH_2$ $C_8F_{17}SO_2NHC_2H_4NH_2$

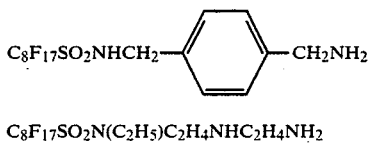

$C_8F_{17}SO_2N(C_2H_5)C_2H_4NHC_2H_4NH_2$

Another class of nonpolymeric cationic fluorinated materials useful in the present invention are the quaternary derivatives of the perfluoroalkanesulfonamidopolymethylenedialkylamine compounds. These derivatives are described in U.S. Pat. No. 2,759,019. They may be represented by the formula $$R_fSO_2N(R^2)R^3N^+R_3^7E^- \quad (XIV)$$

wherein $R_f$, $R^2$, and $R^3$ are as described in formula I, $R^7$ is an alkyl group containing from 1 to 6 carbon atoms and E is an anion. Typical anions include $H_2PO_4^\ominus$, $NO_3^\ominus$ and halogens such as iodide, bromide, and chloride.

Representative examples of perfluoroalkanesulfonamidopolymethylenedialkylamine quaternary derivatives include $C_8F_{17}SO_2N(CH_3)C_2H_4N^+(CH_3)_3 \cdot Cl^-$ $C_8F_{17}SO_2NHC_3H_6N^+(CH_3)_3 \cdot Cl^-$ $C_8F_{17}SO_2NHC_3H_6N^+(CH_3)_2C_2H_4OH \cdot H_2PO_4^-$ Nonfluorinated materials are also useful as nonpolymeric cationic membrane-forming materials in the present invention. Thus, for example, alkyl amines of the formula $C_nH_{2n+1}NH_2$, wherein n is from 4 to 20, have been found useful.

Alkyl guanidines have also been found useful as membrane-forming materials of the present invention. For example, $C_{16}H_{33}NHC(NH)NH_2 \cdot HCl$ has been found useful as a membrane-forming material.

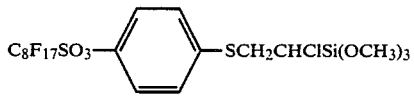

Nonionic Membrane-Forming Materials

Useful nonionic membrane-forming materials are believed to attach to tooth surfaces by interacting with either or both of (i) the hydroxyl groups of the hydroxyapetite (i.e., $C_{10}(PO_4)_6(OH)_2$) or (ii) the hydroxyl groups present on the tooth surfaces from water or saliva in the mouth. In any event, useful nonionic membrane-forming materials may be represented by the formulae $$[R^8]_b-Si-[R^9]_{4-b} \quad (XV)$$

$$[R^{10}]_x-Ti-[OR^{11}]_{4-x} \quad (XVI)$$

$$[R^{12}]_xTi[R^{11}]_{4-x} \quad (XVII)$$

In these formulae $R^8$ is selected from hydrocarbon and fluorocarbon groups or combinations of hydrocarbon and fluorocarbon groups which may contain up to 25 carbon atoms. When $R^8$ contains fluorocarbon terminal groups it is preferred that they be separated from the Si atom by an alkylene group. $R^8$ may be aliphatic, aromatic or a combination of aliphatic and aromatic groups which may contain heteroatoms selected from nitrogen, sulfur, oxygen and silicon. Preferably no two of said hetero atoms are adjacent, and the oxygen atoms present are in the form of ether linkages. $R^9$ is an alkoxy group containing from 1 to 6, and preferably from 1 to 3, carbon atoms. $R^{10}$ is selected from hydrocarbon groups, preferably alkoxy groups, containing from 1 to 20 carbon atoms and preferably from 1 to 10 carbon atoms. $R^{11}$ is selected from hydrocarbon groups of 1 to 20 carbon atoms which may be aliphatic, aromatic or aliphatic and aromatic and which may contain nitrogen, phosphorous, oxygen and sulfur substitution. $R^{12}$ is a heterocyclic group containing carbon, oxygen and hydrogen. The value of b and x is 0, 1, 2 or 3.

One class of materials according to formulae XV and XVI useful in the present invention include fluorocarbon siloxanes of the type described in U.S. Pat. No. 3,442,664 and having the formula $$R_fR^{13}Si(OR^{14})_3 \quad (XVIII)$$

wherein $R_f$ is as defined in formula I, $R^{13}$ is an alkylene group of from 2 to 4 carbon atoms and $R^{14}$ is an alkyl group of from 1 to 4 carbon atoms.

Representative examples of useful fluorocarbon siloxanes according to formula XVIII include $C_8F_{17}CH_2CHClSi(OCH_3)_3$ $C_8F_{17}CH_2CHClSi(OC_2H_5)_3$ Other fluorocarbon siloxanes useful as the membrane-forming material in the present invention include $C_7F_{15}CONHC_3H_6Si(OC_2H_5)_3$ $C_{18}H_{37}\overset{+}{N}(CH_3)_2C_3H_6Si(OCH_3)_3 \; Cl^-$ This last compound is commercially available from Dow Corning Corporation as Q9-5700.

Compounds according to formulae XVI and XVII useful in the invention include the organotitanates. Examples of these compounds include (a) titanium di(dioctylphosphato)oxyacetate.

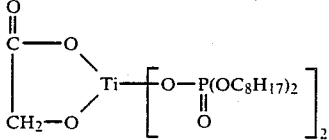

(b) diisostearoyl, ethylenetitanate,

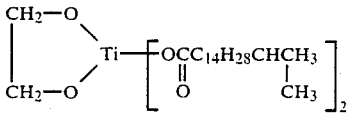

(c) isopropyl, triisostearoyl titanate.

-continued

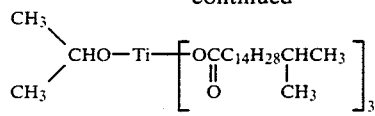

(d) isopropyl, tristearoyl titanate,

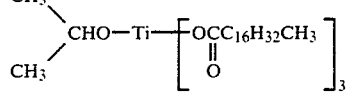

(e) isopropyl, tri(dioctylphosphato) titanate,

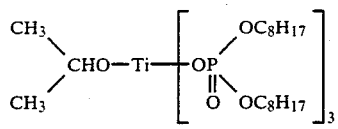

(f) isopropyl, tri(dioctylpropyl pyrophosphato) titanate,

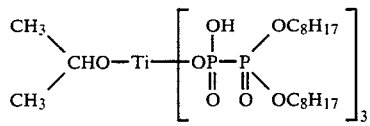

The foregoing titanium compounds are available from Kenrich Petro-chemicals as the Ken-react titanates.

Other ingredients may be added to the compositions of the present invention. For example, therapeutic agents, such as caries prophylactic agents, polishing agents, surfactants, flavoring and sweetening agents, thickening agents and humectants may be included using techniques which are known to the art.

When such other ingredients are employed with (i) the anionic membrane-forming materials or (ii) the cationic membrane-forming materials which have a calcium complexing moiety D, the other ingredients must be substantially free of polyvalent metal atoms, (e.g., calcium, magnesium, etc). These atoms interact with these particular types of membrane-forming materials and prevent them from forming the barrier. Thus while a minor amount of such atoms may be present, the total amount present must not prevent the membrane-forming material from interacting with the teeth. Preferably these compositions are free of polyvalent metal atoms.

With these factors in mind, then, suitable therapeutic agents, such as caries prophylactic agents, include sodium fluoride, stannous fluoride, potassium fluoride, hexylamine hydrofluoride, myristylamine hydrofluoride, betaine fluoride, glycine potassium fluoride, etc. A particularly preferred fluoride is sodium fluoride.

When such other ingredients are employed with (i) the nonionic membrane-forming materials or (ii) the cationic membrane-forming materials which are free from calcium complexing moieties, such ingredients need not be substantially free from polyvalent metal atoms.

The therapeutic agents, when employed, are typically present in sufficient concentration so as to provide an available fluoride ion concentration of up to about 2% by weight, and preferably in the range of about 0.5-2% by weight, of the dentifrice composition. Additionally, it is preferred that the weight ratio of therapeutic ingredient to membrane-forming material be in the range of about 1:0.5 to 1:5 and most preferably in the range of about 1:0.5 to 1:1.

Suitable polishing agents include abrasive materials such as nonionic polymers. Representative of such materials are water-impervious crosslinked thermosetting resins (e.g., the condensation product of melamine and urea with formaldehyde), powdered polymethylmethacrylate and powdered polyethylene. Preferably the polishing agent is not so abrasive so as to scratch or unduly abrade the tooth surface or the dentin. Rather it only cleans the tooth surface. The polishing agents may comprise up to 95% by weight of the dentifrice composition.

Surfactants useful in the present invention include, for example, nonionic surfactants which are known to the art. These materials tyically comprise up to about 5% by weight of the dentifrice composition.

Flavoring and sweetening agents useful in the invention include, for example, the oils of wintergreen, peppermint, spearmint, sassafras and anise. Additionally small amounts of sweetening agents such as saccharin, dextrose, levulose, etc., may also be added to the compositions. The flavoring and sweetening agents may comprise up to about 5% by weight of the dentifrice composition.

Gelling or thickening agents useful in the invention include, for example, water-soluble salts of cellulose ethers such as sodium carboxy methyl cellulose and sodium carboxy methyl hydroxy ethyl cellulose, natural gums such as gum karaya, gum arabic, and gum tragacanth; and colloidal magnesium-aluminum silicate or finely divided silica. Such thickening agents may comprise up to about 5% by weight of the dentifrice composition.

When provided in solution, dentifrices of the present invention typically comprise a solution of the membrane-forming material in water or a mixture of water and an alcohol. Typically the alcohol is a lower alkanol (e.g., ethanol, propanol, etc.). These compositions are particularly useful as mouthwashes or rinses.

The present invention is further illustrated in the following examples.

EXAMPLE 1

This example demonstrates that compositions of the invention form substantially continuous barriers that reduce the elution of a previously applied fluoride treatment from teeth.

Separate bovine central incisors were used in the tests. A flat surface was provided on each tooth by first polishing each with 240 grit silicon carbide abrasive paper; and then with 400 grit silicon carbide abrasive paper. The teeth were then given a 5 minute soak with a 2% by weight solution of sodium fluoride (NaF) in deionized water. One-half of the number of the teeth were then given a 5 minute soak with a 1% by weight solution of membrane forming material $(C_{16}H_{33}O)_2$-POOH, in deionized water. The remaining teeth were give no treatment with the membrane-forming composition. All of the teeth were then tested for initial water contact angle, initial fluoride level, water contact angle after a 26 hour water soak and fluoride content after a 26 hour water soak.

The water contact angle was measured by placing a drop of water on the flat polished surface of the tooth using a Model 710 "Hamilton" microliter syringe. The drop was then photographed using a Polaroid ® camera which had a telescopic lens. The maximum perpendicular height (h) of the drop from the surface of the tooth to the top of the drop and the maximum length (l) of the drop in contact with the surface of the tooth were measured. These values were used to calculate the contact angle—by inserting them in the formula $(\tan \theta/2) = 2h/l$.

As the water contact angle increases the water repellancy of the surfaces increases. High water contact angles (e.g., at least about 70°) are characteristic of the anoinic membrane-forming materials.

The fluoride content was measured with an electron microprobe Model 400 available from Material Analysis Co. This was a destructive test so that duplicate sets of teeth were tested in order to determine the initial fluoride content and the fluoride content after water soak. The results obtained are given in Table V.

TABLE V

| TOOTH TREATMENT | INITIAL | | 26 HOUR WATER SOAK | |
|---|---|---|---|---|
| | CONTACT ANGLE (°) | FLUORIDE ON TOOTH (COUNTS/SEC) | CONTACT ANGLE (°) | FLUORIDE ON TOOTH (COUNTS/SEC) |
| A. NaF | 21 | 1.7 | — | — |
| B. NaF + $(C_{16}H_{33}O)_2POOH$ Composition | 100.4 | 1.2 | — | — |
| C. NaF | 34 | — | 35.4 | 0.5 |
| D. NaF + $(C_{16}H_{33}O)_2POOH$ Composition | 89 | — | 66.2 | 0.9 |

Comparison of treatments A and B shows the dramatic increase in water contact angle caused by the addition of the membrane-forming material $(C_{16}H_{33}O)_2POOH$. Comparison of treatments C and D shows that, even after soaking the teeth for 26 hours in water, the membrane remains on the surface and that it substantially reduces elution of the initial fluoride treatment.

EXAMPLE 2

Bovine teeth were prepared and treated with NaF as described in Example 1. Certain of the teeth were then soaked for 5 minutes with compositions containing various membrane-forming materials. Each of the teeth were then soaked in separate 100 ml deionized water baths for 24 hours. The teeth were removed from the baths and each bath was then analyzed for fluoride ion content using a fluoride ion electrode. The results of these tests are set forth in Table VI.

TABLE VI

| TOOTH TREATMENT | FLUORIDE CONTENT IN WATER (µg/ml) |
|---|---|
| A 2% NaF | 1.04 |
| B 2% NaF + 0.5% $C_8F_{17}SO_2N(C_2H_5)C_2H_4OPO(OH)_2$ + 97.5% deionized water | 0.55 |
| C 2% NaF | 0.72 |

TABLE VI-continued

| TOOTH TREATMENT | FLUORIDE CONTENT IN WATER (µg/ml) |
|---|---|
| D 2% NaF + 1% Polyacrylic Acid (CH$_2$CH) + 97% deionized water COOH | 0.21 |
| E NaF + 1% $[C_{18}H_{37}\overset{+}{N}(CH_3)_2C_3H_6Si(OCH_3)_3]Cl^-$ + 97% deionized water | 0.43 |

Comparison of treatments A and B (run simultaneously) graphically illustrates the decrease in elution of the NaF as a result of the presence of the membrane-forming material. Comparison of treatments D and E with treatment C (run simultaneously but at a different time than tests A and B) further graphically illustrate the decrease in elution of the NaF as a result of the presence of the membrane-forming material.

EXAMPLE 3

This example demonstrates the durability of the membrane. Bovine central incisors were prepared and the initial water contact angle measured as described in Example 1. The teeth were then soaked for 5 minutes with 0.1% by weight solutions of various membrane-forming materials in deionized water. The water contact angle was then measured after the teeth had been soaked in deionized water for 10 and 60 minutes and 24 hours. The results are given in Table VII.

TABLE VII

| MEMBRANE-FORMING MATERIAL | WATER CONTACT ANGLE (°) | | | |
|---|---|---|---|---|
| | INITIAL | 10 MIN SOAK | 60 MIN SOAK | 24 HOUR SOAK |
| 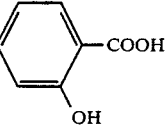 | 33.4 | 90 | 91 | 92.8 |
| $C_8F_{17}C_{10}H_{20}COOH$ | 38.5 | 114 | 102 | 110.4 |
| $C_8F_{17}SO_2N(C_2H_5)C_2H_4OPO(OH)_2$ | 34.2 | 101.5 | 93 | 50 |

The high water contact angles, even after 24 hours of water soaking, demonstrate that the membranes retain their integrity for extended periods of time.

EXAMPLE 4

The procedures of Example 3 were repeated except that the teeth were given a fluoride treatment before being soaked for 5 minutes with a 0.1% by weight solution of membrane-forming material in deionized water. The fluoride treatment consisted of a 5 minute soak with an acidulated phosphate fluoride which comprised 40 grams (g) of NaF, 11.8 ml of HF, 126 ml of $H_3PO_4$ and 1400 ml of deionized water. The results of the water contact angle measurements are given in Table VIII.

TABLE VIII

| MEMBRANE-FORMING MATERIAL | WATER CONTACT ANGLE (°) | | | | |
|---|---|---|---|---|---|
| | Initial* | 4 Min | 5 Hrs | 24 Hrs | 5 days |
| $C_8F_{17}SO_2H(C_2H_5)C_2H_4OPO(OH)_2$ | 43.6 | 101.4 | 94 | 104 | 87.6 |
| Triethanolamine salt of stearic acid | 38 | 102 | 78.4 | 80 | — |

This data demonstrates the durability of membranes formed from membrane-forming materials according to the invention.

EXAMPLE 5

Bovine central incisors were sequentially polished with 120 grit, 400 grit and 600 grit SiC abrasive papers so as to obtain a smooth, flat, uniform surface. The polished teeth were exposed to fluoride solution. One half of the number of the teeth were then used as controls while the remaining teeth were coated with various membrane-forming materials by dipping the teeth in an aqueous solution (0.5% by weight) for 5 minutes and then air-drying the treated teeth. All of the teeth were then exposed to water by soaking them in two separate 5 microliter portions of water for 15 minutes each. The fluoride remaining on the teeth after soaking was recovered by etching the teeth with a 5 microliter portion of 0.5M perchloric acid which had been further diluted to 100 microliters by volume. The amount of fluoride recovered was determined by the hanging-drop fluoride electrode technique (P. Venkateswarlu, Analytical Chemistry: 46 878, 1974).

The amount of fluoride retained on the coated teeth and the control teeth was then compared by dividing the amount retained on the coated teeth by the amount retained on the control teeth.

The fluoride treatments, membrane-forming materials and results of the hanging drop test are set forth in Table IX.

TABLE IX

| FLUORIDE TREATMENT | MEMBRANE-FORMING MATERIAL | FLUORIDE RETENTION (Ratio Coated: Control) |
|---|---|---|
| 4% NaF, 5 min. | $C_8F_{17}(CH_2)_{10}COOH$ | 2.3 |
| 4% NaF, 5 min. | Protamine Sulfate | 18 |
| 4% NaF, 5 min. | $(C_{16}H_{33}O)_2POOH$ | 1.7 |
| 4% NaF, 5 min. | $(CH_3)_2CHOTi[OCOC_{16}H_{32}CH_3]_3$ | 1.4 |
| 4% NaF, 5 min. | $(CH_3)_2CHOTi[OCOC_{16}H_{32}CH_3]_3$ | 1.8 |
| 5% $SnF_2$, 5 min. | $(CH_3)_2CHOTi[OCOC_{16}H_{32}CH_3]_3$ | 1.2 |
| | | 2.6 |
| | | 2.3 |
| | | 2.8 |
| | | 3.0 |

As can be seen from the data, the compositions of the invention substantially reduce the elution of a previously applied fluoride.

EXAMPLE 6

Example 5 was repeated except a different water washing technique was employed. In this example the water washing comprised drip washing the teeth with water for a period of time and followed by etching the teeth to recover the retained fluoride. Two etchings with the perchloric acid were performed. The first gave a measure of the fluoride retained by the coated teeth while the second gave a measure of the depth of fluoride treatment.

The fluoride treatments, membrane-forming materials and results of the hanging drop test are set forth in Table X.

TABLE X

| FLUROIDE TREATMENT | MEMBRANE-FORMING MATERIAL | WASHING TIME (HRS) | $L^1$ | $L^2$ |
|---|---|---|---|---|
| 4% NaF, 5 min. | $C_8F_{17}(CH_2)_{10}COOH$ | 36 | 2.2 | 1.7 |
| | | | 9.7 | 1.3 |
| 4% NaF, 5 min. | $(C_{16}H_{33}O)_2POOH$ | 36 | 2.5 | 1.6 |
| | | | 1.2 | 1.3 |
| 4% NaF, 5 min. | $(C_3H)_2CHOTi[OCOC_{16}H_{32}CH_3]_3$ | 36 | 7.5 | 1.5 |
| | | | 1.9 | 1.4 |
| 4% NaF, 5 min. | $C_8F_{17}SO_2N(C_2H_5)CH_2COOK$ | 36 | 1.4 | 1.0 |
| $Na_2PO_3F$ (0.1% F) | $C_8F_{17}SO_2N(C_2H_5)CH_2COOK$ | 44 | 1.7 | 1.0 |
| | | | 2.3 | 1.3 |
| | | | 1.7 | 1.7 |
| $SnF_2$ (0.1% F) 3 min. | $C_8F_{17}SO_2N(C_2H_5)CH_2COOK$ | 60 | 1.8 | 1.4 |
| | | | 1.4 | 1.3 |

$L^1$ = first etching
$L^2$ = second etching

As can be seen from the data, treated teeth are resistant to elution of a previously applied fluoride treatment.

What is claimed is:

1. A dentifrice composition for substantially effectively coating previously fluoride-treated teeth and thereby reducing elution of said fluoride from said teeth, said composition comprising:
   a fluoride-containing caries prophylactic agent; and
   at least about 0.05% by weight of a nonionic water-dispersible, membrane-forming material which, when applied to the surface of said previously fluoride-treated teeth in an oral environment, forms a substantially continuous hydrophobic barrier thereon which substantially reduces the elution of said previously applied fluoride from said teeth and which is selected from the group consisting of $(R^8)_b Si(R^9)_{4-b}$ $(R^{10})_x Ti(OR^{11})_{4-x}$ $R^{12}—Ti—R^{11}_2$ wherein $R^8$ is selected from hydrocarbon and fluorocarbon groups which contain up to 25 carbon atoms optionally substituted by chlorine; $R^9$ is an alkoxy group containing from 1 to 6 carbon atoms; $R^{10}$ is selected from hydrocarbon groups containing from 1 to 20 carbon atoms; $R^{11}$ is selected from hydrocarbon groups of from 1 to 20 carbon atoms which may contain nitrogen, phosphorous, oxygen and sulfur substitution; $R^{12}$ together with the Ti atom forms a five-membered saturated heterocyclic ring containing two oxygens, carbon and hydrogen, wherein the two oxygens are attached to the Ti atom and wherein one carbon may bear an oxo group; b and x are selected from 0, 1, 2 and 3.

2. A dentifrice composition according to claim 1 wherein said membrane-forming material has the formula $(R^8)_b Si(R^9)_{4-b}$ wherein $R^8$ has the formula $R_f R^{14}—$; wherein $R_f$ is a stable, inert, fluorinated, saturated, nonpolar aliphatic radical containing from about 4 to 16 carbon atoms, and $R^{14}$ is an alkylene group of from 1 to 4 carbon atoms optionally substituted by chlorine; and $R^9$ has the formula $—OR^{15}$, wherein $R^{15}$ is an alkyl group of from 1 to 4 carbon atom.

3. A dentifrice composition according to claim 2 wherein said membrane-forming material is selected from $C_8F_{17}CH_2CHClSi(OCH_3)_3$ $C_8F_{17}CH_2CHClSi(OCH_2H_5)_3$.

4. A dentifrice composition for substantially effectively coating previously fluoride-treated teeth and thereby reducing elution of said fluoride from said teeth, said composition comprising a fluoride-containing caries prophylactic agent; and at least about 0.05% by weight of a nonionic water dispersible, membrane-forming material which, when applied to the surface of said previously fluoride-treated teeth in an oral environment, forms a substantially continuous hyrophobic barrier thereon which substantially reduces the elution of said previously applied fluoride from said teeth and which is selected from the group

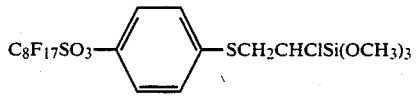

$C_7F_{15}CONHC_3H_6Si(OC_2H_5)_3$.

5. A dentifrice composition according to claim 1 wherein said membrane-forming material is selected from titanium di(dioctylphosphato)oxyacetate; diisostearoyl, ethylene titanate; isopropyl, triisostearoyl titanate; isopropyl, tristearoyl titanate; isopropyl, tri(dioctylphosphato)titanate; and isopropyl, tri(dioctylpropylpyrophosphato)titanate.

6. A method of substantially reducing elution of a therapeutic agent previously applied to teeth which comprises the steps of applying said therapeutic agent to teeth, and applying a dentifrice composition to said treated teeth, wherein said dentifrice composition comprises (1) at least one ingredient selected from the group consisting of therapeutic agents, polishing agents, surfactants, flavoring agents, sweetening agents, thickening agents and humectants, and (2) at least 0.05% by weight of a nonionic, water-dispersible, membrane-forming material which, when applied to the surface of the teeth in an oral environment, forms a substantially continuous hydrophobic barrier thereon which substantially reduces the elution of said previously applied therapeutic agent from said teeth, and which is selected from the group consisting of $(R^8)_b Si(R^9)_{4-b}$ $(R^{10})_x Ti(OR^{11})_{4-x}$ $(R^{12})_x Ti(R^{11})_{4-x}$ wherein $R^8$ is selected from hydrocarbon and fluorocarbon groups which contain up to 25 carbon atoms optionally substituted by chlorine; R is an alkoxy group containing from 1 to 6 carbon atoms; $R^{10}$ is selected from hydrocarbon groups containing from 1 to 20 carbon atoms; $R^{11}$ is selected from hydrocarbon groups of from 1 to 20 carbon atoms; $R^{12}$ is a heterocyclic group containing only carbon, oxygen and hydrogen; b and x are selected from 0, 1, 2 and 3.

* * * * *

UNITED STATES PATENT AND TRADEMARK OFFICE
CERTIFICATE OF CORRECTION

PATENT NO. : 4,510,127

DATED : April 9, 1985

INVENTOR(S) : Robert W. H. Chang

It is certified that error appears in the above-identified patent and that said Letters Patent is hereby corrected as shown below:

Col. 20, line 44, "R" should read --$R^9$--.

Signed and Sealed this

First Day of October 1985

[SEAL]

*Attest:*

*Attesting Officer*

DONALD J. QUIGG

*Commissioner of Patents and Trademarks—Designate*